United States Patent
Vautravers et al.

(10) Patent No.: US 10,875,821 B2
(45) Date of Patent: Dec. 29, 2020

(54) PROCESS FOR THE PREPARATION OF ALPHA, BETA UNSATURATED ALDEHYDES BY OXIDATION OF ALCOHOLS IN THE PRESENCE OF A LIQUID PHASE

(71) Applicant: BASF SE, Ludwigshafen am Rhein (DE)

(72) Inventors: Nicolas Vautravers, Ludwigshafen am Rhein (DE); Joaquim Henrique Teles, Ludwigshafen am Rhein (DE); Andreas Keller, Ludwigshafen am Rhein (DE); Kirsten Braunsmann, Ludwigshafen am Rhein (DE); Andreas Jörg Ufer, Ludwigshafen am Rhein (DE); Stefan Bauer, Ludwigshafen am Rhein (DE); Marco Bosch, Ludwigshafen am Rhein (DE); Vera Luense, Ludwigshafen am Rhein (DE); Joseph John Zakzeski, Ludwigshafen am Rhein (DE); Michaela Fenyn, Lugwigshafen am Rhein (DE)

(73) Assignee: BASF SE

( * ) Notice: Subject to any disclaimer, the term of this patent is extended or adjusted under 35 U.S.C. 154(b) by 0 days.

(21) Appl. No.: 16/494,910

(22) PCT Filed: Mar. 12, 2018

(86) PCT No.: PCT/EP2018/056008
§ 371 (c)(1),
(2) Date: Sep. 17, 2019

(87) PCT Pub. No.: WO2018/172110
PCT Pub. Date: Sep. 27, 2018

(65) Prior Publication Data
US 2020/0010393 A1    Jan. 9, 2020

(30) Foreign Application Priority Data

Mar. 20, 2017 (EP) ..................................... 17161798
Jun. 27, 2017 (EP) ..................................... 17178052
Dec. 21, 2017 (EP) ..................................... 17209505

(51) Int. Cl.
| | |
|---|---|
| C07C 45/39 | (2006.01) |
| B01J 23/00 | (2006.01) |
| B01J 23/42 | (2006.01) |
| B01J 37/00 | (2006.01) |
| B01J 37/02 | (2006.01) |
| B01J 37/06 | (2006.01) |
| B01J 37/08 | (2006.01) |
| B01J 37/16 | (2006.01) |

(52) U.S. Cl.
CPC .............. C07C 45/39 (2013.01); B01J 23/42 (2013.01); B01J 37/009 (2013.01); B01J 37/0215 (2013.01); B01J 37/0236 (2013.01); B01J 37/06 (2013.01); B01J 37/08 (2013.01); B01J 37/16 (2013.01)

(58) Field of Classification Search
CPC ........... C07C 45/38; C07C 45/39; B01J 23/42
See application file for complete search history.

(56) References Cited

U.S. PATENT DOCUMENTS

| | | | |
|---|---|---|---|
| 6,013,843 A | 1/2000 | Aquila et al. | |
| 6,476,260 B1 | 11/2002 | Herrmann et al. | |

FOREIGN PATENT DOCUMENTS

| | | |
|---|---|---|
| EP | 0881206 A1 | 12/1998 |
| FR | 2386509 A1 | 11/1978 |
| WO | WO-99/18058 A1 | 4/1999 |
| WO | WO-9918058 A1 | 4/1999 |
| WO | WO-2004/060844 A1 | 7/2004 |
| WO | WO-2004060844 A1 | 7/2004 |
| WO | WO-2008/037693 A1 | 4/2008 |
| WO | WO-2008037693 A1 | 4/2008 |

OTHER PUBLICATIONS

International Search Report for PCT/EP2018/056008 dated May 9, 2018.
Written Opinion of the International Searching Authority for PCT/EP2018/056008 dated May 9, 2018.
Anderson, et al., "Selective Oxidation of Alcohols to Carbonyl Compounds and Carboxylic Acids with Platinum Group Metal Catalysts", Advanced Synthesis & Catalysis, vol. 345, Issue 4, Mar. 19, 2003, pp. 517-523.
Chen, et al., "A Recoverable Sandwich Phosphorotungstate Stabilized Palladium (0) Catalyst for Aerobic Oxidation of Alcohols in Water", Applied Catalysis A: General, vol. 523, Aug. 5, 2016, pp. 304-311.
European Search Report for EP Patent Application No. 17161798.8, dated May 15, 2017, 3 pages.
Heyns, et al., "Katalytische oxydation von primären und sekundären hydroxylverbindungen mit sauerstoff am platinkontakt in flüssiger phase : Über katalytische oxydationen—XIV", Tetrahedron, vol. 9, Issue 1-2, 1960, pp. 67-75.
Huang, et al., "Sustainable catalytic oxidation of alcohols over the interface between air and water", Green Chemistry, vol. 17, Issue 4, 2015, pp. 2325-2329.
International Search Report for PCT Patent Application No. PCT/EP2018/056008, dated May 9, 2018, 4 pages.

(Continued)

*Primary Examiner* — Sikarl A Witherspoon
(74) *Attorney, Agent, or Firm* — Faegre Drinker Biddle & Reath

(57) ABSTRACT

Process for the preparation of alpha, beta unsaturated aldehydes by oxidation of alcohols in the presence of a liquid phase wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide.

17 Claims, 2 Drawing Sheets

(56) References Cited

OTHER PUBLICATIONS

Figure 1:
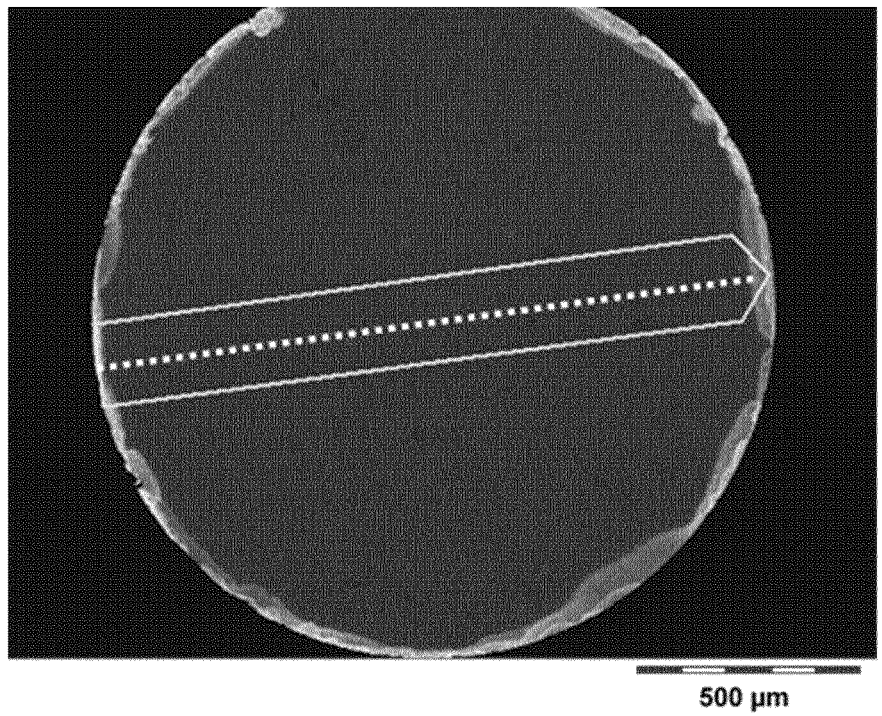

Kon, et al., "Oxidation of allylic alcohols to α,β-unsaturated carbonyl compounds with aqueous hydrogen peroxide under organic solvent-free conditions", Chemical Communications, Issue 42, 2007, pp. 4399-4400.

Lee, et al., "Aspects of allylic alcohol oxidation—a bimetallic heterogeneous selective oxidation catalyst", Green Chemistry, vol. 2, Issue 6, 2000, pp. 279-282.

Liu, et al., "Yolk-Shell Hybrid Materials with a Periodic Mesoporous Organosilica Shell: Ideal Nanoreactors for Selective Alcohol Oxidation", Advanced Functional Materials, vol. 22, Issue 3, Feb. 8, 2012, pp. 591-599.

Ma, et al., "Palladium nanoparticles confined in the nanocages of SBA-16: Enhanced recyclability for the aerobic oxidation of alcohols in water", Journal of Molecular Catalysis A: Chemical, vol. 331, Issue 1-2, Oct. 1, 2010, pp. 78-85.

Tonucci, et al., "Catalytic aerobic oxidation of allylic alcohols to carbonyl compounds under mild conditions", Green Chemistry, vol. 11, Issue 6, 2009, pp. 816-820.

The following pictures display the Pt distribution in the catalyst of example C6.

500 µm

BSE

The Y-axis shows the local Pt-concentration in weight% measured by EDX, while the X-axis shows the position at which the measurement was taken. The distances are taken along the dotted line in the upper picture and the zero point is at the left side.

PROCESS FOR THE PREPARATION OF ALPHA, BETA UNSATURATED ALDEHYDES BY OXIDATION OF ALCOHOLS IN THE PRESENCE OF A LIQUID PHASE

CROSS-REFERENCE TO RELATED APPLICATIONS

This application is a national stage application (under 35 U.S.C. § 371) of PCT/EP2018/056008, filed Mar. 12, 2018, which claims benefit of European Application No. 17209505.1 filed Dec. 21, 2017, European Application No. 17178052.1, filed Jun. 27, 2017, and European Application No. 17161798.8, filed Mar. 20, 2017, all of which are incorporated herein by reference in their entirety.

The present invention relates to a process for preparing alpha, beta unsaturated aldehydes, such as in particular, prenal (3-methyl-2-butenal) by oxidation of alcohols in the presence of a liquid phase. More specifically, the invention relates to a process for preparing alpha, beta unsaturated aldehydes, such as, in particular prenal (3-methyl-2-butenal) by oxidation of alcohols in the presence of a catalyst and a liquid phase, wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide.

TECHNICAL BACKGROUND

Prenal is an important chemical intermediate especially for the preparation of terpene-based fragrances, such as citral, and for the preparation of vitamins, such as vitamin E, and therefore is of great technical and economic importance.

The most common procedures for preparing prenal use prenol (3-methyl-2-buten-1-ol) or isoprenol (3-methyl-3-buten-1-ol) as starting compounds. Thus, EP 0 881 206 describes the oxidation of these starting compounds with oxygen in the gas phase using a silver catalyst. The selectivity of this approach could be improved by further developing the catalytic system, as disclosed e.g. in WO 2008/037693. However, in order to obtain sufficient conversion rates and selectivity it is necessary to carry out the procedure in the gas phase at temperatures of about 360° C. while maintaining short contact times. This is required, on the one hand, to ensure adequate reactivity and, on the other hand, to prevent decomposition reactions of the sensitive reactants and products. These conditions can only be accomplished by using expensive equipment.

WO 99/18058 discloses a process for the aerobic oxidation of primary alcohols, such as hexanol in the absence of solvents.

Processes for preparing alpha, beta unsaturated aldehydes by oxidation in the liquid phase using organic solvents are described in the prior art: Tetrahedron, Vol 9 (1960), p. 72 Table 1 describes the oxidation of tiglyl alcohol or geraniol in n-heptane with $PtO_2$ and oxygen. According to p. 74 (e) 0.32 g tiglyl alcohol in 30 cc n-heptane are employed, which amounts to 1.06 weight-% of reactant (alcohol). Tiglylaldehyd is obtained with a yield of 77% after 2 hours, resulting in a space-time-yleld of 4.08 g/l/h. Adv. Synth. Catal. 345 (2003), p. 5197-523, Table 2 describes the oxidation of geraniol with oxygen and a Pt/Bi/C catalyst. The reaction was conducted with 15 mmol reactant in 30 ml toluene, which amounts to 8.88 weight-% reactant (alcohol). At a conversion of 100% and after 6 hours, this results in a space-time-yleld of 14.67 g/l/h. Green Chemistry, 2 (2000) describes on page 280, table 1 entry 2 the aerobic selective oxidation of crotyl alcohol over a Pt/Bi/graphite catalyst. The reaction was conducted with 5 mmol substrate in 60 ml solvent (ethanol). This amounts to 0.75 weight-% of crotyl alcohol. Crotorialdehyde is obtained with a yield of 42% after 15 hours, resulting in a space-time-yleld of 0.16 g/l/h. Table 1 entry 7 describes the aerobic selective oxidation of trans-hex-2-en-1-ol. The reaction was conducted with 5 mmol substrate in 60 ml solvent (ethanol). This amounts to 1.0 weight-% of alcohol. The aldehyde is obtained with a yield of 57% after 15 hours, resulting in a space-time-yleld of 0.3 g/l/h.

The oxidation of prenol to prenal in an aqueous liquid phase is described in Green Chem. 2015, 17, 2325-2329; Green Chem. 2009, 11, 816-820; Adv. Funct. Mater. 2012, 22, 591-599 as well as in Molecular Catalysis A: Chemical 2010, 331 (1-2): Green Chem. 2015, 17, p. 2327 Table 1 describes the oxidation of prenol using 1 mmol substrate in 10 ml water. At 45° C. a yield of 91% is obtained after a reaction time of 3 hours. This amounts to 0.86 weight-% of alcohol and results in a space-time-yield of 2.6 g/l/h. Adv. Funct. Mater. 2012, 22, 591-599, table 5, entry 4 describes the oxidation of prenol to prenal, wherein 4.3 weight-% of alcohol is used. The reaction is conducted for 8 hours with a conversion of 53% and a selectivity of 99%, resulting in a space-time-yield of 2.8 g/l/h. Molecular Catalysis A: Chemical 2010, 331 (1-2), table 4, entry 6 describes the oxidation of prenol to prenal, wherein 4.3 weight % of alcohol is used. The reaction is conducted for 12 hours with a conversion of 89.5% and a selectivity of 99%, resulting in a space-time-yield of 3.1 g/l/h.

Chem. Commun. (2007) 4399-4400 describes the formation of alpha, beta unsaturated aldehydes with aqueous hydrogen peroxide as oxidant in the presence of Pt black catalyst under organic solvent free conditions. Table 1 discloses this reaction for a list of alcohols: Entry 7 discloses the oxidation of 3-methyl-2-butenol to 3-methyl-2-butenal with 5% hydrogen peroxide as oxidant and Pt black as catalyst. The reaction is conducted with 10 mmol alcohol, 5% $H_2O_2$ and Pt black in a 100:110:1 molar ratio for 3 h. This amounts to 10 weight-% of alcohol. At a yield of 91% this results in a space-time-yield of 31 g/l/h.

It was an objective of the invention to provide a simple and efficient process for preparing alpha, beta unsaturated aldehydes of formula (I), in particular prenal, which is suitable for industrial scale preparations. The process should be easy to handle, provide high yields and high selectivity of the aldehyde to be prepared, thus avoiding over-oxidation to the corresponding acid. Moreover, the use of toxic or expensive reagents should be avoided. Moreover, the process should allow high space-time-yields (STY), which are of major importance for the economic suitability in industrial scale processes. The space-time-yield (STY) is defined as the amount of product obtained per reaction volume per hour of reaction, expressed as g/l/h. The reaction volume is the volume of the reactor in which the reaction takes place. In case the reaction is conducted in a cylindrical reactor, the reaction volume is the volume of the cylindrical reactor in which the reaction takes place. Of special interest are processes which allow high space-time-yields in a reaction time, in which at least 40%, preferably at least 50% conversion is achieved. Furthermore, it was desired to provide a process which enables easy recovery of the aldehyde.

Moreover, the process should allow a high specific activity (SA), which is of major importance for the economic suitability in industrial scale processes. The specific activity (SA) is defined as the amount of product obtained per amount of catalytically active metal per hour of reaction, expressed as g/g/h. Of special interest are processes which allow high specific activities in a reaction time, in which at least 40%, preferably at least 50% conversion is achieved.

SUMMARY OF THE INVENTION

It has now been found that the objectives are achieved by an oxidation in the presence of a catalyst and in the presence of a liquid phase, wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide, all weight-% based on the total weight of the liquid phase, determined at a temperature of 20° C. and a pressure of 1 bar.

It has surprisingly been found that the alpha, beta unsaturated aldehydes of formula (I) can be obtained with excellent yield and selectivity with the process according to the invention. The process according to the invention is further associated with a series of advantages. The process according to the invention enables the preparation of alpha, beta unsaturated aldehydes of formula (I) with high yield and high selectivity under mild conditions, both of temperature and pressure, while requiring only moderate to low amounts of catalyst. The process can be conducted with no or low amounts of organic solvent, thus avoiding or minimizing environmentally problematic waste streams. The process also allows a simple isolation of the desired aldehyde. A further advantage of the process of the invention is that the desired aldehyde is obtained in a high concentration in the reaction mixture, thus minimizing down-stream isolation steps. The process according to the invention leads to space-time-yields, which are higher than the space-time-yields that are obtainable with processes according to the prior art. With the process according to the invention specific activities can be achieved, which are higher than the specific activities that are possible with processes according to the prior art.

Therefore, the present invention relates to a process for the preparation of alpha, beta unsaturated aldehydes of general formula (I)

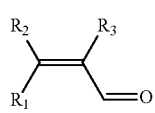

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl;

by oxidation of alcohols of general formula (II)

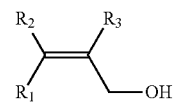

wherein $R_1$, $R_2$ and $R_3$ have the meaning as given above in the presence of a catalyst and in the presence of a liquid phase,
  wherein the liquid phase contains 0.1 to less than 25 weight-% water and
  wherein the liquid phase contains at least 25 weight-% of alcohol(s) of general formula (II) and alpha, beta unsaturated aldehyde(s) of general formula (I) and
  wherein the oxidant is oxygen and/or hydrogen peroxide, all weight-% based on the total weight of the liquid phase, determined at a temperature of 20° C. and a pressure of 1 bar.

A BRIEF DESCRIPTION OF THE FIGURES

Figure 2:
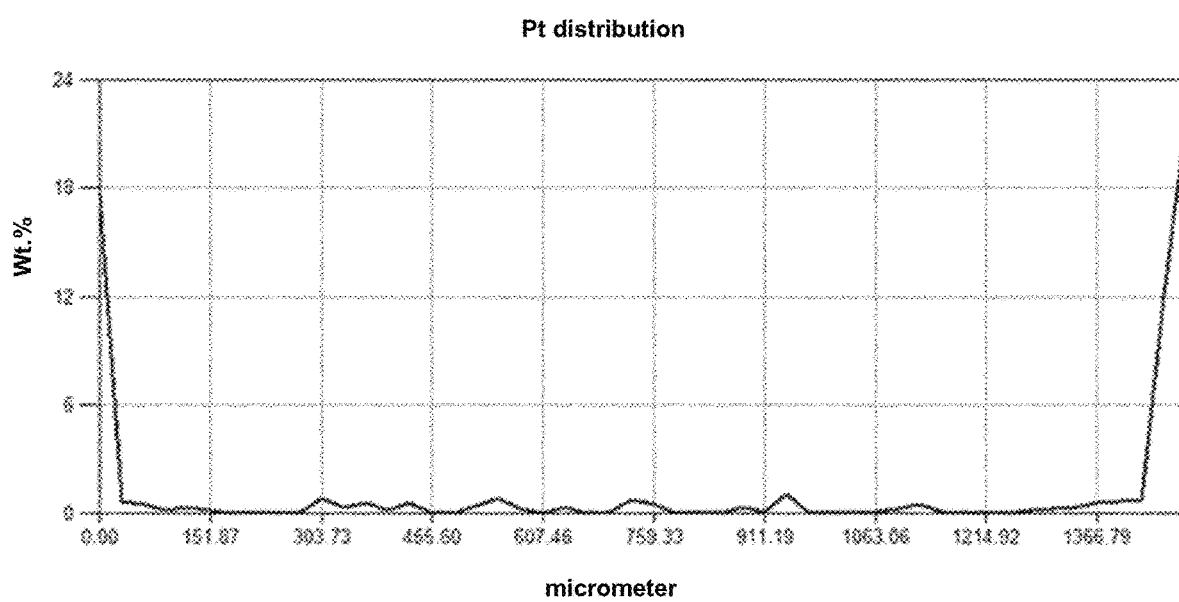

FIGS. 1 and 2 illustrate the Pt distribution in the catalyst of example C6. In FIG. 2 the Y-axis shows the local Pt-concentration in weight % measured by EDX, while the X-axis shows the position at which the measurement was taken. The distances are taken along the dotted line in FIG. 1 and the zero point is at the left side.

GENERAL DEFINITIONS

In the context of the present invention, the terms used generically are, unless otherwise stated, defined as follows:
The prefix $C_x$-$C_y$ denotes the number of possible carbon atoms in the particular case.

Alkyl and also all alkyl moieties in radicals derived therefrom, such as e.g. alkoxy, acyl, acyloxy, refers to saturated, straight-chain or branched hydrocarbon radicals having x to y carbon atoms, as denoted in $C_x$-$C_y$.

Thus, the term $C_1$-$C_4$-alkyl denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term $C_1$-$C_6$-alkyl denotes a linear or branched alkyl radical comprising 1 to 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term alkenyl denotes mono- or poly-, in particular monounsaturated, straight-chain or branched hydrocarbon radicals having x to y carbon atoms, as denoted in $C_x$-$C_y$ and a double bond in any desired position, e.g. $C_2$-$C_6$-alkenyl, or $C_2$-$C_4$ alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3- butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Each double bond in the alkenyl moiety can independently of each other be present in the E- or the Z-configuration.

The term substituents denotes radicals selected from the group consisting of $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl.

The term halogen denotes in each case fluorine, bromine, chlorine or iodine, especially fluorine, chlorine or bromine.

The term alkoxy denotes straight-chain or branched saturated alkyl radicals comprising from 1 to 6 ($C_1$-$C_6$-alkoxy) or 1 to 4 ($C_1$-$C_4$-alkoxy) carbon atoms, which are bound via an oxygen atom to the remainder of the molecule, such as methoxy, ethoxy, n-propoxy, 1-methylethoxy (isopropoxy), n-butyloxy, 1-methylpropoxy (sec-butyloxy), 2-methylpropoxy (isobutyloxy) and 1,1-dimethylethoxy (tert-butyloxy).

The term ($C_1$-$C_6$-alkoxy)carbonyl denotes alkoxy radicals having from 1 to 6 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl, n-pentyloxycarbonyl and n-hexyloxycarbonyl.

The term $C_1$-$C_6$ acyl denotes straight-chain or branched saturated alkyl radicals comprising from 1 to 6 carbon atoms, which are bound via a carbonyl group to the remainder of the molecule. Examples thereof are formyl, acetyl, propionyl, 2-methylpropionyl, 3-methylbutanoyl, butanoyl, pentanoyl, hexanoyl.

The term $C_1$-$C_6$ acyloxy denotes $C_1$-$C_6$ acyl radicals, which are bound via an oxygen atom to the remainder of the molecule. Examples thereof are acetoxy, propionyloxy, butanoyloxy, pentanoyloxy, hexanoyloxy.

The term aryl denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

Selectivity is defined as the number of moles of the alpha, beta unsaturated aldehyde of the general formula (I) formed divided by the number of moles of the alcohol of the general formula (II) that were consumed. The amounts of alpha, beta unsaturated aldehyde of the general formula (I) formed and of alcohol of the general formula (II) consumed can easily be determined by a GC analysis as defined in the experimental section.

The terms "conducted" and "performed" are used synonymously.

EMBODIMENTS OF THE INVENTION

The remarks made below regarding preferred embodiments of the reactant(s) and product(s) and the process according to the invention, especially regarding preferred meanings of the variables of the different reactant(s) and product(s) and of the reaction conditions of the process, apply either taken alone or, more particularly, in any conceivable combination with one another.

Alcohol(s) of General Formula (II)

Reactant(s) of the process of the invention are alcohol(s) of general formula (II)

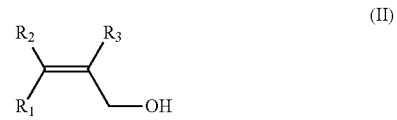

(II)

wherein $R_1$, $R_2$ and $R_3$, independently of one another, are selected from
hydrogen;
$C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl; and
$C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl;

The terms "reactant(s)" and "alcohol(s) of general formula (II)" are used synonymously. The term alcohol(s) encompasses one alcohol as well as a mixture of more than one alcohol according to formula (II).

In one embodiment of the invention alcohol(s) of general formula (II) are used, wherein $R_3$ is H.

In one embodiment of the invention alcohol(s) of general formula (II) are used, wherein $R_1$, $R_2$ and $R_3$, independently of one another, are selected from the group consisting of H, $C_1$-$C_6$-alkyl and $C_2$-$C_6$-alkenyl.

In one embodiment of the invention alcohol(s) of general formula (II) are used, wherein $R_1$, $R_2$ and $R_3$, independently of one another, are selected from the group consisting of H, $C_1$-$C_6$-alkyl and $C_2$-$C_4$-alkenyl.

In one embodiment of the invention alcohol(s) of general formula (II) are used, wherein $R_1$, $R_2$ and $R_3$, independently of one another, are selected from the group consisting of H, $C_1$-$C_6$-alkyl and $C_2$-$C_6$-alkenyl.

In one embodiment of the invention alcohol(s) of general formula (II) are used, wherein $R_1$, $R_2$ and $R_3$, independently of one another, are selected from the group consisting of $C_1$-$C_4$-alkyl and $C_2$-$C_4$-alkenyl.

In one embodiment of the invention alcohol(s) of general formula (II) are used, wherein $R_1$, $R_2$ and $R_3$, independently of one another, are selected from the group consisting of H, $CH_3$ and $C_2H_5$.

In one embodiment of the invention alcohol(s) of general formula (II) are used, wherein $R_1$, $R_2$ and $R_3$, independently of one another, are selected from the group consisting of H and $CH_3$.

In one embodiment of the invention an alcohol of the general formula (II) is used, wherein $R_1$ is H and $R_2$ and $R_3$ are $CH_3$.

In one embodiment of the invention an alcohol of the general formula (II) is used, wherein $R_3$ is H and $R_1$ and $R_2$ are $CH_3$ (=3-Methyl-2-buten-1-ol, prenol).

In one embodiment of the invention an alcohol of the general formula (II) is used, wherein $R_1$ is $CH_3$, $R_3$ is H and $R_2$ is $C_6$-Alkenyl, preferably 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; Each double bond in the alkenyl moiety can independently of each other be present in the E- as or the Z-configuration.

In one embodiment of the invention an alcohol of the general formula (II) is used, wherein $R_2$ is $CH_3$, $R_3$ is H and $R_1$ is $C_6$-Alkenyl, preferably 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; Each double bond in the alkenyl moiety can independently of each other be present in the E- as or the Z-configuration.

In one embodiment of the invention the alcohol of the general formula (II) is selected from the group consisting of (2E)-3,7-dimethylocta-2,6-dien-1-ol, (2Z)-3,7-dimethylocta-2,6-dien-1-ol, 3-methylbut-2-en-1-ol, (E)-2-methylbut-2-en-1-ol and (Z)-2-methylbut-2-en-1-ol.

In one embodiment of the invention the alcohol of the general formula (II) is 3-methylbut-2-en-1-ol. In case the alcohol of general formula (II) is 3-methylbut-2-en-1-ol, the invention also encompasses the embodiment that 2-methyl-3-buten-2-ol (dimethylvinylcarbinol, DMVC) is added to the reaction and subsequently isomerized to 3-methylbut-2-en-1-ol.

In one embodiment of the invention the alcohol of the general formula (II) is a mixture of (2E)-3,7-dimethylocta-2,6-dien-1-ol and (2Z)-3,7-dimethylocta-2,6-dien-1-ol.

Alpha, Beta Unsaturated Aldehyde(s) of General Formula (I)

Product(s) of the process of the invention are alpha, beta unsaturated aldehyde(s) of general formula (I)

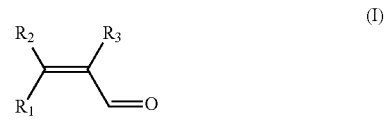

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl.

The terms "product(s)" and "alpha, beta unsaturated aldehyde(s) of general formula (I)" are used synonymously. The term "aldehyde(s)" encompasses one aldehyde as well as a mixture of more than one aldehyde according to formula (I).

It has surprisingly been found that the process according to the invention can be performed in the presence of a liquid phase wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide, all weight-% based on the total weight of the liquid phase, determined at a temperature of 20° C. and a pressure of 1 bar.

The process according to the invention is conducted in the presence of a liquid phase. The liquid phase consists of all components of the reaction which are liquid at 20° C. and a pressure of 1 bar.

All weight-% of the liquid phase referred to in the process according to the invention are based on the total weight of the liquid phase, determined at a temperature of 20° C. and a pressure of 1 bar.

Depending on the catalyst and oxidant used, the process according to the invention is conducted in a liquid phase (catalyst and oxidant are part of the liquid phase, homogenous catalyzed process) or at the interphase between liquid phase and the solid catalyst (heterogeneous catalyzed process). The term "in the presence of a liquid phase" encompasses the process in a liquid phase as well as the process at the interphase.

In case the process is conducted as a heterogeneous catalyzed process, the solid catalyst is not liquid at a temperature of 20° C. and a pressure of 1 bar and is therefore by definition not included in the weight-% of the liquid phase.

The liquid phase can consist of one or more, e.g. two or three distinct liquid phases. The number of liquid phases can be chosen by a man skilled in the art, dependent for example on the choice and concentration of the alcohol(s) of general formula (II) or on optional solvent(s).

The process according to the invention can be conducted in the presence of a liquid phase, which consists of one liquid phase (mono-phase system). The process according to the invention can be conducted in the presence of a liquid phase, which consists of more than one, e.g. two, three or more distinct liquid phases (multi-phase system).

In case the process according to the invention is conducted in the presence of a liquid phase which consists of one liquid phase, the liquid phase contains 0.1 to less than 25 weight-% water and at least 25 weight-% of alcohol(s) of general formula (II) and alpha, beta unsaturated aldehyde(s) of general formula (I).

In case the process according to the invention is conducted in the presence of a liquid phase which consists of more than one liquid phase, at least one distinct liquid phase contains 0.1 to less than 25 weight-% water and at least 25 weight-% of alcohol(s) of general formula (II) and alpha, beta unsaturated aldehyde(s) of general formula (I).

Water

In case the process according to the invention is conducted in the presence of a liquid phase which consists of one liquid phase, the liquid phase contains 0.1 to less than 25 weight-% water.

In case the process according to the invention is conducted in the presence of a liquid phase which consists of more than one liquid phase, at least one distinct liquid phase contains 0.1 to less than 25 weight-% water.

As water is generated in the process of the invention, the man skilled in the art will choose the water content of the reaction so that it will not exceed 25 weight-% during the course of the reaction.

The following preferred ranges for the water content of a liquid phase apply for the liquid phase for mono-phase systems or for the at least one distinct liquid phase for multi-phase systems.

In one embodiment of the invention the process is performed in the presence of a liquid phase, which contains 0.5 to 20 weight-%, preferably 1.0 to 15 weight-% water based on the total weight of the liquid phase. In a further embodiment, the process can be performed in the presence of a liquid phase, which contains 1.0 to 10 weight-%, preferably 1.0 to 8 weight-%, preferably 1.0 to 6 weight-%, preferably 1.0 to 5 weight-%, preferably 1.0 to 3 weight-% water based on the total weight of the liquid phase. All weight-% of water are based on the total weight of the liquid phase for mono-phase systems or the at least one distinct liquid phase for multi-phase systems.

In one embodiment of the invention the process is performed in the presence of a liquid phase, which contains 0.1 to 20 weight-%, preferably 0.1 to 10 weight-% water based on the total weight of the liquid phase. All weight-% of water are based on the total weight of the liquid phase for mono-phase systems or the at least one distinct liquid phase for multi-phase systems.

Reactant(s) and Product(s)

The process according to the invention is performed in the presence of a liquid phase which contains at least 25 weight-% of reactant(s) (alcohol(s) of general formula (II)) and product(s) alpha, beta unsaturated aldehyde(s) of general formula (I)).

In case the process according to the invention is conducted in the presence of a liquid phase which consists of one liquid phase, the liquid phase contains at least 25 weight-% of reactant(s) and product(s).

In case the process according to the invention is conducted in the presence of a liquid phase which consists of more than one liquid phase, at least one distinct liquid phase contains at least 25 weight-% of reactant(s) and product(s).

The following preferred ranges for the weight-% of reactant(s) and product(s) of a liquid phase apply for the liquid phase for mono-phase systems or for the at least one distinct liquid phase for multi-phase systems.

In one embodiment of the invention the liquid phase contains at least 30 weight-%, preferably at least 50 weight-%, preferably at least 60 weight-%, preferably at least 70 weight-%, preferably at least 75 weight-%, preferably at least 80 weight-%, preferably at least 85 weight-%, preferably at least 90 weight-%, preferably at least 95 weight-% of reactant(s) and product(s), based on the total weight of the liquid phase for mono-phase systems or the at least one distinct liquid phase for multi-phase systems.

In one embodiment of the invention the liquid phase contains 25 to 99.9 weight-% of reactant(s) and product(s) based on the total weight of the liquid phase for mono-phase systems or the at least one distinct liquid phase for multi-phase systems.

In one embodiment of the invention the liquid phase contains at least 25 to 50 weight-%, preferably 26 to 45 weight-%, preferably 30 to 40 weight-% of reactant(s) and product(s) based on the total weight of the liquid phase for mono-phase systems or the at least one distinct liquid phase for multi-phase systems.

In one embodiment of the invention, the liquid phase contains 50 to 99.9 weight-%, preferably 50 to 99.5 weight-%, preferably 60 to 99 weight-%, more preferably 70 to 90 weight-%, more preferably 75 to 80 weight-% of reactant(s) and product(s) based on the total weight of the liquid phase for mono-phase systems or the at least one distinct liquid phase for multi-phase systems.

In one embodiment of the invention, the liquid phase contains 25 to 99.9 weight-% of reactant(s) and product(s) and 0.1 to less than 25 weight-% water.

In one embodiment of the invention, the liquid phase contains at least 50 weight-% of reactant(s) and product(s) and 0.1 to less than 25 weight-% water, preferably 0.1 to 20 weight-% water, preferably 0.1 to 10 weight-% water.

In one embodiment of the invention, the liquid phase contains at least 60 weight-% of reactant(s) and product(s) and 0.1 to less than 25 weight-% water, preferably 0.1 to 20 weight-% water, preferably 0.1 to 10 weight-% water.

In one embodiment of the invention, the liquid phase contains at least 70 weight-% of reactant(s) and product(s) and 0.1 to less than 25 weight-% water, preferably 0.1 to 20 weight-% water, preferably 0.1 to 10 weight-% water.

In one embodiment of the invention, the liquid phase contains at least 80 weight-% of reactant(s) and product(s) and 0.1 to less than 25 weight-%, preferably 0.1 to 20 weight-% water, preferably 0.1 to 10 weight-% water.

Solvent(s)

The process according to the invention can be carried out in the presence of a liquid phase which essentially consist of reactant(s), product(s), water and oxidant(s).

The process according to the invention can be carried out as a heterogeneous catalyzed process in the presence of a liquid phase which essentially consist of reactant(s), product(s), water and oxidant(s).

The process according to the invention can be carried out as a homogenous catalyzed process in the presence of a liquid phase which essentially consist of reactant(s), product(s), water and oxidant(s) and catalyst(s).

In these embodiments the liquid phase contains no solvent.

The term "solvent" encompasses any component other than reactant(s), product(s), water and possibly oxidant(s) or possibly catalyst(s) which is liquid at a temperature of 20° C. and a pressure of 1 bar and which is thus part of the liquid phase.

It is therefore one of the advantages of the present invention, that the process can be performed in the presence of a liquid phase, which comprises less than 75 weight-%, preferably less than 70 weight-% solvent based on the total weight of the liquid phase.

In case a solvent is employed, a suitable solvent can be selected depending on the reactant(s), product(s), catalyst(s), oxidant(s) and reaction conditions. The term "solvent" encompasses one or more than one solvents.

The following preferred ranges for the solvent content of a liquid phase apply for the liquid phase (for mono-phase systems) or for the at least one distinct liquid phase (for multi-phase systems).

In a preferred embodiment of the invention the process is performed in a liquid phase, which contains less than 70 weight-%, preferably less than 60 weight-%, preferably less than 50 weight-%, preferably less than 40 weight-%, preferably less than 30 weight-%, more preferably less than 20 weight-%, more preferably less than 10 weight-% solvent based on the total weight of the liquid phase (for mono-phase systems) or the at least one distinct liquid phase (for multi-phase systems).

Advantageously the process according to the invention can be performed in the presence of a liquid phase, which contains less than 5 weight-% solvent based on the total weight of the liquid phase (for mono-phase systems) or the at least one distinct liquid phase (for multi-phase systems). In one embodiment of the invention the process is performed in the presence of a liquid phase which contains less than 3 weight-%, preferably less than 1 weight-% of solvent. In one embodiment of the invention the process is performed in the presence of a liquid phase which contains no solvent.

In case a solvent is employed, suitable solvents are for example protic or aprotic solvents.

In case a solvent is employed, it has been found to be advantageous to use an aprotic organic solvent for the reaction of the alcohol(s) of general formula (II).

In case a solvent is employed, solvents are preferred that have a boiling point above 50° C., for instance in the range of 50 to 200° C., in particular above 65° C., for instance in the range of 65 to 180° C., and specifically above 80° C., for instance in the range of 80 to 160° C.

Useful aprotic organic solvents here include, for example, aliphatic hydrocarbons, such as hexane, heptane, octane, nonane, decane and also petroleum ether, aromatic hydrocarbons, such as benzene, toluene, the xylenes and mesitylene, aliphatic $C_3$-$C_8$-ethers, such as 1,2-dimethoxyethane (DME), diethylene glycol dimethyl ether (diglyme), diethyl ether, dipropyl ether, methyl isobutyl ether, tert-butyl methyl ether and tert-butyl ethyl ether, dimethoxymethane, diethoxymethane, dimethylene glycol dimethyl ether, dimethylene glycol diethyl ether, trimethylene glycol dimethyl ether, trimethylene glycol diethyl ether, tetramethylene glycol dimethyl ether, cycloaliphatic hydrocarbons, such as cyclohexane and cycloheptane, alicyclic $C_3$-$C_6$-ethers, such as tetrahydrofuran (THF), tetrahydropyran, 2-methyltetrahydrofuran, 3-methyltetrahydrofuran, 1,3-dioxolane, and 1,4-dioxane, 1,3,5-trioxane, short-chain ketones, such as acetone, ethyl methyl ketone and isobutyl methyl ketone, $C_3$-$C_6$-esters such as methyl acetate, ethyl acetate, methyl propionate, dimethyloxalate, methoxyacetic acid methyl ester, ethylene carbonate, propylene carbonate, ethylene glycol diacetate and diethylene glycol diacetate, $C_3$-$C_6$-amides such as dimethylformamide (DMF) and dimethylacetamide and N-methylpyrrolidone (NMP), dimethyl sulfoxide (DMSO), $C_3$-$C_6$-nitriles such as acetonitrile, propionitrile or mixtures of these solvents with one another.

According to an embodiment of the present invention those of the aforementioned aprotic solvents are preferred that have a boiling point above 50° C., for instance in the range of 50 to 200° C., in particular above 65° C., for instance in the range of 65 to 180° C., and specifically above 80° C., for instance in the range of 80 to 160° C.

More preferably the solvent, if employed, is selected from the group consisting of 1,2-dimethoxyethane (DME), diethylene glycol dimethyl ether (diglyme), diethoxymethane, dimethylene glycol dimethyl ether, tri-methylene glycol dimethyl ether, tetramethylene glycol dimethyl ether, 1,3-dioxolane, 1,4-dioxane, 1,3,5-trioxane, dimethylacetamide, methyl acetate, dimethyloxalate, methoxyacetic acid methyl ester, ethylene carbonate, propylene carbonate, ethylene glycol diacetate and diethylene glycol diacetate, toluene, the xylenes, mesitylene, $C_7$-$C_{10}$-alkanes, such as octane or nonane, THF, 1,4-dioxane and mixtures thereof, and specifically selected from toluene, ortho-xylene, meta-xylene, para-xylene and mesitylene.

In a preferred embodiment, the solvent, if employed, is selected from solvents which have a water solubility of greater 150 g/l at 20° C. In a preferred embodiment the solvent, if employed, is selected from solvents which have a vapour pressure of below 100 mbar at 20° C.

In a preferred embodiment the solvent, if employed, is selected from the group consisting of diethylene glycol dimethyl ether, triethylene glycol dimethylether and dimethylacetamide, polyoxymethylene dimethylether of general formula (III) $H_3C-O-(CH_2O)_n-CH_3$ wherein n=3 to 8, dimethyloxalate, methoxyacetic acid methyl ester, ethylene carbonate, propylene carbonate, ethylene glycol diacetate and diethylene glycol diacetate.

Oxidant(s)

The process according to the invention can be performed with oxygen and/or hydrogen peroxide as oxidant. Oxygen can be used undiluted or diluted. The oxygen can be diluted with other inert gases like $N_2$, Ar or $CO_2$, e.g in the form of air. In a preferred embodiment of the invention oxygen is used undiluted. Hydrogen peroxide can be used as an aqueous solution, wherein the concentration of the aqueous solution will be chosen by a man skilled in the art so as not to exceed the maximum water content of the liquid phase.

In a preferred embodiment of the invention oxygen is used as oxidant.

Catalyst

The process according to the invention can be performed as a heterogeneous catalyzed process or as a homogeneous catalyzed process.

In a preferred embodiment of the invention the process is conducted as a heterogeneous catalysed process. In such a heterogeneous catalyzed process the catalyst and reactant(s)/product(s) are in different phases, which are in contact with each other. The reactant(s)/product(s) are in the liquid phase, whereas the catalyst will be, at least partially in a solid phase. The reaction will take place at the interphase between liquid phase and solid phase.

The process according to the invention is carried out in the presence of a catalyst. The catalyst comprises at least one catalytically active metal. In the process according to the invention the catalytically active metal can be selected from the elements selected from the groups 8, 9, 10 and 11 of the periodic table (according to IUPAC nomenclature). The elements of group 8, 9, 10 and 11 of the periodic table comprise iron, cobalt, nickel, ruthenium, rhodium, palladium, osmium, iridium, platinum, copper, silver and gold.

In a preferred embodiment, the catalytically active metal is selected from elements from the groups 10 and 11 of the periodic table (according to IUPAC nomenclature).

In a preferred embodiment, the catalytically active metal is selected from elements selected from the group consisting of platinum, palladium and gold.

In a preferred embodiment of the invention the catalytically active metal is platinum.

The catalytically active metal can be used in any form, e.g. unsupported or on a support. The catalytically active metal can be used in an unsupported form, for example as a powder, a mesh, a sponge, a foam or a net. In a preferred embodiment, the catalytically active metal is on a support.

The catalyst can optionally comprise one or more so called promotors, which enhance the activity of the catalytically active metal. Examples for such promotors are bismuth (Bi), antimony (Sb), lead (Pb), cadmium (Cd), tin (Sn), tellurium (Te), cerium (Ce), selenium (Se) or thallium (Tl).

In a preferred embodiment, the catalyst comprises at least one promotor selected from the group consisting of bismuth (Bi), antimony (Sb), lead (Pb), cadmium (Cd), tin (Sn) and tellurium (Te). In a preferred embodiment, the catalyst comprises at least one promotor selected from the group consisting of bismuth (Bi), lead (Pb) and cadmium (Cd). In a preferred embodiment, the catalyst comprises bismuth (Bi).

The promotors can for example be employed as metals, nitrates, acetates, sulphates, citrates, oxides, hydroxides or chlorides and mixtures thereof.

In a preferred embodiment, the catalytically active metal is platinum and the promotor is bismuth.

In case a promotor is employed, suitable molar ratios of the catalytically active metal and the promotor are in the range from 1:0.01 to 1:10, preferably 1:0.5 to 1:5, more preferably from 1:0.1 to 1:3.

The promotors can for example be present on the support or can be added separately to the process.

The term "on a support" encompasses that the catalytically active metal and/or promotor can be located on the outer surface of a support and/or on the inner surface of a support. In most cases, the catalytically active metal and/or promotor will be located on the outer surface of a support and on the inner surface of a support.

In case the catalytically active metal is on a support, the catalyst comprises the catalytically active metal, the support and optionally promotors.

In one embodiment of the invention, the process is conducted as a batch process and the molar ratio of the catalytically active metal to the alcohol(s) of general formula (II) is in the range 0.0001:1 to 1:1, more preferably in the range 0.001:1 to 0.1:1 and even more preferably in the range 0.001:1 to 0.01:1.

In one embodiment of the invention, the process is conducted as a continuous process and the catalyst load (defined as total amount of alcohol of general formula (II)/total amount of catalytically active metal in the reactor/time unit) is in the range 0.01 to 100 g of alcohol(s) of general formula (II) per g of catalytically active metal per hour, more preferably in the range 0.1 to 20 g of alcohol(s) of general formula (II) per g of catalytically active metal per hour.

In one embodiment of the invention, the process is conducted as a continuous process and the catalyst load (defined as total amount of alcohol of general formula (II)/total amount of catalytically active metal in the reactor/time unit) is in the range 30 to 40000 g of alcohol(s) of general formula (II) per g of catalytically active metal per hour, more preferably in the range 1000 to 9000, more preferably in the range 1200 to 5000, preferably 1500 to 4000, preferably in the range of 1650 to 3500 g of alcohol(s) of general formula (II) per g of catalytically active metal per hour.

In case the catalytically active metal is on a support, the support can for example be a powder, a shaped body or a mesh, for example a mesh of iron-chromium-aluminium (FeCrAl), that was tempered in the presence of oxygen (commercially available under the trademark Kanthal®).

In a preferred embodiment of the invention the catalytically active metal is employed on a support. In a preferred embodiment, the catalytically active metal is employed on a support and the support is selected from the group consisting of powders and shaped bodies. In case a support in the form of a powder is employed, such powders usually have a particle size in the range of 1 to 200 μm, preferably 1 to 100 μm. The shaped bodies can for example be obtained by extrusion, pressing or tableting and can be of any shape such as for example strands, hollow strands, cylinders, tablets, rings, spherical particles, trilobes, stars or spheres. Typical dimensions of shaped bodies range from 0.5 mm to 250 mm.

In a preferred embodiment, the support has a diameter from 0.5 to 20 mm, preferably from 0.5 to 10 mm, more preferably from 0.7 to 5 mm, more preferably from 1 to 2.5 mm, preferably 1.5 to 2.0 mm.

In a preferred embodiment, the support is obtained by extrusion and is in the form of a strand or hollow strand. In one embodiment, a support is employed with strand diameters from 1 to 10 mm, preferably 1.5 to 5 mm. In one embodiment, a support is employed with strand lengths from 2 to 250 mm, preferably 2 to 100 mm, preferably 2 to 25 mm, more preferably 5 to 10 mm. In one embodiment, a support is employed with a strand diameter of 1 to 2 mm and strand lengths of 2 to 10 mm.

In a preferred embodiment, the catalytically active metal is employed on a support, wherein the support is selected from the group consisting of carbonaceous and oxidic materials.

Suitable support materials are for example carbonaceous or oxidic materials. A preferred carbonaceous support is activated carbon. The surface area of carbonaceous support materials preferably is at least 200 $m^2/g$, preferably at least 300 $m^2/g$. In case a carbonaceous support is used an activated carbon with a surface area of at least 300 $m^2/g$ is preferred. In a preferred embodiment, the catalytically active metal (preferably platinum) is employed on an activated carbon support, preferably with an activated carbon support with a surface area of at least 300 $m^2/g$.

In case an oxidic support is used, the oxides of the following elements can be used: Al, Si, Ce, Zr, Ti, V, Cr, Zn, Mg. The invention also encompasses the use of mixed oxides comprising two or more elements. In one embodiment of the invention mixed oxides are used as support selected from the group consisting of (Al/Si), (Mg/Si) and (Zn/Si) mixed oxides. In a preferred embodiment, an oxidic support is used, selected from the group consisting of aluminum oxide and silicium dioxide. Aluminium oxide can be employed in any phase, such as alpha aluminium oxide ($\alpha$-$Al_2O_3$), beta aluminium oxide ($\beta$-$Al_2O_3$), gamma aluminium oxide ($\gamma$-$Al_2O_3$), delta aluminium oxide ($\delta$-$Al_2O_3$), eta aluminium oxide ($\eta$-$Al_2O_3$), theta aluminium oxide ($\theta$-$Al_2O_3$), chi aluminium oxide ($\chi$-$Al_2O_3$), kappa aluminium oxide ($\kappa$-$Al_2O_3$) and mixtures thereof.

In a preferred embodiment, the oxidic support is selected from the group consisting of alpha aluminium oxide ($\alpha$-$Al_2O_3$), beta aluminium oxide (ß-$Al_2O_3$), gamma aluminium oxide ($\gamma$-$Al_2O_3$), delta aluminium oxide ($\delta$-$Al_2O_3$), and theta aluminium oxide ($\theta$-$Al_2O_3$).

In a preferred embodiment, the oxidic support is selected from the group consisting of alpha aluminium oxide ($\alpha$-$Al_2O_3$), beta aluminium oxide (ß-$Al_2O_3$) and gamma aluminium oxide ($\gamma$-$Al_2O_3$).

In one embodiment, the oxidic support is gamma aluminium oxide ($\gamma$-$Al_2O_3$).

Commercially available gamma aluminium oxide ($\gamma$-$Al_2O_3$), can be treated at temperatures from 500 to 700° C., preferably at temperatures from 550° C. to 600° C. to ensure that the complete $Al_2O_3$ is in the gamma-phase.

In one embodiment the oxidic supports can have a BET-surface area (BET, Brunnauer-Emmet-Teller determined according to DIN 66131 by $N_2$ adsorption at 77 K) from 0.1 to 500 $m^2/g$. Preferably the oxidic supports have a BET-surface area of at least 0.1 $m^2/g$, preferably at least 1 $m^2/g$, preferably at least 10 $m^2/g$, more preferably of at least 30 $m^2/g$, more preferably of at least 50 $m^2/g$, more preferably of at least 75 $m^2/g$, preferably of at least 100 $m^2/g$, preferably of at least 150 $m^2/g$ especially preferred of at least 200 $m^2/g$.

In a further embodiment, the oxidic support has a BET-surface area of 1 $m^2/g$ to 50 $m^2/g$. In a further embodiment, the oxidic support has a BET-surface area of 10 $m^2/g$ to 300 $m^2/g$, preferably of 20 to 100 $m^2/g$. In a further embodiment, the oxidic support has a BET-surface area of 100 $m^2/g$ to 300 $m^2/g$, preferably 150 to 300 $m^2/g$.

In a preferred embodiment, the support is $Al_2O_3$ with a BET-surface area of 100 to 300 $m^2/g$.

In one embodiment, the catalyst comprises platinum on a support.

In one embodiment, the catalyst comprises platinum on a support, wherein the support is selected from carbonaceous and oxidic materials.

In one embodiment, the catalyst comprises platinum on a support, wherein the support is selected from carbonaceous and oxidic materials, and wherein the oxidic material is selected from the group consisting of oxides of the elements selected from the group consisting of Al, Ce, Zr, Ti, V, Cr, Zn and Mg.

In one embodiment, the catalyst comprises of platinum on a support, wherein the support is selected from carbonaceous materials and oxidic materials, and wherein the oxide is selected from the group consisting of oxides of the elements selected from the group consisting of Al, Ce, Zr and Ti.

In a preferred embodiment, the catalyst is selected from the group consisting of platinum on carbon (Pt/C) and platinum on aluminium oxide (Pt/$Al_2O_3$).

In a preferred embodiment, the catalyst comprises platinum on aluminium oxide, wherein the aluminium oxide is selected from the group consisting of alpha aluminium oxide ($\alpha$-$Al_2O_3$), beta aluminium oxide (ß-$Al_2O_3$), gamma aluminium oxide ($\gamma$-$Al_2O_3$), delta aluminium oxide ($\delta$-$Al_2O_3$), eta aluminium oxide ($\eta$-$Al_2O_3$), theta aluminium oxide ($\theta$-$Al_2O_3$), chi aluminium oxide ($\chi$-$Al_2O_3$) and kappa aluminium oxide ($\kappa$-$Al_2O_3$).

In case the catalytically active metal is on a support, the content of the catalytically active metal of the catalyst usually is in the range of 0.1 to 20 weight-%, preferably 0.1 to 15 weight-%, preferably in the range of 0.5 to 10 weight-%.

In case the catalytically active metal is employed on a support, the catalyst can be prepared for example by a deposition-reduction method, in which a metal compound is first deposited on a support and then reduced to the catalytically active metal. The reduction can be performed with any known method, for example in the gas phase or in the liquid phase.

In a preferred embodiment of the invention, the catalyst is obtainable by
a) providing a support
b) providing a metal compound
c) depositing the metal compound on the support
d) optionally calcinating the so obtained catalyst precursor
e) reducing the catalyst precursor
f) optionally recovering the catalyst.

In a preferred embodiment of the invention, the catalyst is obtained by
a) providing a support
b) providing a metal compound
c) depositing the metal compound on the support
d) optionally calcinating the so obtained catalyst precursor
e) reducing the catalyst precursor
f) optionally recovering the catalyst.

Step a) Providing a Support

A suitable support is provided, for example by adding the support in form of a powder or a shaped body directly to a reactor vessel or by providing the support as a slurry (in case the support is in form of a powder).

Step b) Providing a Metal Compound

The metal compound is a precursor of the catalytically active metal. The catalytically active metal is obtained by reduction of the metal compound.

The metal compound can be employed as solution, for example as an aqueous solution of a water-soluble salt of the metal compound or as a non-aqueous solution. The metal compound can also be employed as a colloid in which the non-dissolved metal compound is dispersed in a liquid phase.

In a preferred embodiment, the metal compound is employed as a salt. Depending on the solubility of the salt, aqueous or non-aqueous solutions can be employed.

Suitable salts of the metal compound include nitrates, acetates, sulphates, citrates, oxides, hydroxides and chlorides and combinations thereof. Preferably water-soluble salts are used.

In a preferred embodiment, the metal compound is selected from the group consisting of platinum salts. Depending on the solubility of the platinum salt, aqueous or non-aqueous solutions of the platinum salt can be employed. Examples for suitable platinum salts are $H_2PtCl_6$, $Pt(NH_3)_2(NO_3)_2$, $Pt(NO_2)_2(NH_3)_2$/$NH_4OH$, $Pt(NO_3)_2$, platinum hydroxides such as $Pt(OH)_2$, $Pt(OH)_4$, or $H_2Pt(OH)_6$, all of which can be stabilized in amines, for example in monoethanolamine, $PtO_2$, bis(2,4-pentanedionato)Platinum (II)= $Pt(C_5H_7O_2)_2$, $K_2PtCl_4$, $NaPtCl_4$, $(NH_4)_2PtCl_4$.

In a preferred embodiment, the platinum salt is selected from the group consisting of $H_2PtCl_6$, $Pt(NH_3)_2(NO_3)_2$, $Pt(NO_2)_2(NH_3)_2$/$NH_4OH$ and $Pt(NO_3)_2$.

Generally, the deposition step c) will be performed prior to the reduction step e). The invention also encompasses the embodiment that the catalytically active metal can be reduced in situ from a metal compound and then deposited on the support.

In case promotors are employed, they can for example be employed as promotor compounds, which are subsequently converted (by oxidation and/or reduction) to the promotors. The promotor compound can be employed as solution, for example as an aqueous solution of a water-soluble salt of the promotor compound or as a non-aqueous solution of the promotor compound. The promotor compound can also be employed as a colloid in which the non-dissolved promotor compound is dispersed in a liquid phase.

Suitable salts of the promotor compound include nitrates, acetates, sulphates, citrates, oxides, hydroxides and chlorides and combinations thereof. Preferably water-soluble salts are used.

In case promotor compounds are employed, they can be added to the metal compound. In this embodiment, the metal compound and the promotor compound are deposited together on the support. In an alternative embodiment, the metal compound and the promotor compound can be deposited separately on the support.

After the one or more deposition step(s), both promotor compound and metal compound are then converted to promotor and catalytically active metal.

In a preferred embodiment, the promotor compound is selected from the group consisting of Bi salts, Cd salts and Pb salts.

Step c) Deposition Step

The deposition of the metal compound on the support can be performed with any known method, for example by chemical or physical vapour deposition or by contacting and mixing the support with the metal compound (=immersion) or by spraying the metal compound on the support.

In a preferred embodiment, the deposition is performed by immersion and/or spraying.

In case the deposition is performed by immersion or by spraying, the metal compound can be employed as solution or as colloid or as a colloid which is generated in situ during the immersion or spraying. The deposition by immersion or spraying can be performed at a temperature of 1 to 100° C. The pH value at which the deposition step is performed can be chosen depending on the metal compound used. The deposition can be performed from 0.1 to 24 hours, usually from 0.5 to 2 hours. The so obtained catalyst precursor can optionally be dried and/or calcined prior to the reduction step.

In case the deposition step is performed by immersion or by spraying, the volume of the solution or colloid of the metal compound is ideally chosen, so that at least 90%, preferably 100% of the pore volume of the support will be filled with the solution or colloid (so called "incipient-wetness" method). The concentration of the metal compound is ideally chosen so that, alter deposition and reduction, a catalyst with the desired content of catalytically active metal is obtained.

The deposition step can be conducted in one step or in multiple, consecutive steps. The deposition step can also be performed as a combination of spraying and immersion.

The catalyst precursor can then be recovered by suitable separation means such as filtration and/or centrifugation. The catalyst precursor can then be washed with water, preferably until a conductivity of less than 400 µS/cm, preferably less than 200 µS/cm is obtained.

In one embodiment, a drying step and/or a calcination step d) can be performed subsequent to the deposition step c).

The calcination step d) can be performed in customary furnaces, for example in rotary furnaces, in chamber furnaces, in tunnel furnaces or in belt calciners.

The calcination step d) can be performed at temperatures from above 200° C. to 1150° C., preferably from 250 to 900° C., preferably from 280° C. to 800° C. and more preferably from 500 to 800° C., preferably from 300° C. to 700° C. The calcination is suitably conducted for 0.5 to 20 hours, preferably from 0.5 to 10 hours, preferably from 0.5 to 5 hours.

The calcination of the catalyst precursor in step d) mainly serves the purpose to stabilize the metal compound (and if present also the promotor compound) deposited on the support and to remove undesired components.

Step e) Reduction Step

The so obtained catalyst precursor can then be reduced, for example by treatment with a gas (gas phase reduction) or by treatment of the catalyst precursor with a solution of a reducing agent (liquid phase reduction).

The gas phase reduction of the catalyst precursor can be performed by treating the catalyst precursor with hydrogen and/or CO. The hydrogen and/or CO can further comprise at least one inert gas, such as for example helium, neon or argon, $N_2$, $CO_2$ and/or lower alkanes, such as methane, ethane, propane and/or butane. Preferably $N_2$ is employed as the inert gas. The gas phase reduction can be performed at temperatures from 30° C. to 200° C., preferably from 50° C. to 180° C., more preferably from 60 to 130° C. Usually the gas phase reduction is performed over a period from 1 to 24 hours, preferably 3 to 20 hours, more preferably 6 to 14 hours.

The liquid phase reduction of the catalyst precursor is performed by treating the catalyst precursor with a solution of a reducing agent. Suitable reducing agents are quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hyposphosphites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $LiBH_4$, $NaBH_4$, $NaBH_3CN$, $KBH_4$, $LiBH(C_2H_5)_3$; diboran ($B_2H_6$); lithium aluminium hydride ($LiAlH_4$); formaldehyde; N-vinyl pyrrolidone (NVP), polyvinyl-pyrrolidone (PVP); phenol; sodium thiocyanate; iron(II) sulfate; sodium amalgam; zinc mercury amalgam.

The liquid phase reduction can be performed at a temperature from 10 to 95° C., preferably from 50 to 90° C. The pH of the reduction step can be chosen depending on the reducing agent used.

In a preferred embodiment, the reduction step is performed by treatment of the catalyst precursor with a solution of a reducing agent.

In a preferred embodiment, the reduction step is performed by treatment of the catalyst precursor with a solution of a reducing agent, wherein the reducing agent is selected from the group consisting of quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hyposphoshites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $NaBH_4$, $NaBH_3CN$, $KBH_4$, $LiBH(C_2H_5)_3$; diboran ($B_2H_6$); lithium aluminium hydride ($LiAlH_4$); formaldehyde; N-vinyl pyrrolidone (NVP), polyvinyl-pyrrolidone (PVP); phenol; sodium thiocyanate; iron(II) sulfate; sodium amalgam; zinc mercury amalgam.

In a preferred embodiment, the reduction step is performed by treatment of the catalyst precursor with a solution of a reducing agent, wherein the reducing agent is selected from the group consisting of sodium formate, sodium citrate, sodium ascorbate, polyols, reducing sugars, formaldehyde, methanol, ethanol and 2-propanol.

The catalyst can then be recovered by suitable separation means such as filtration and/or centrifugation. Typically, the catalyst is then washed with water, preferably until a conductivity of less than 400 µS/cm, preferably less than 200 µS/cm is obtained.

Drying steps can be performed for example subsequent to step c) and/or subsequent to step e). The drying of the catalyst precursor obtained in step c) or of the catalyst obtained in step e) can generally be performed at temperatures above 60° C., preferably above 80° C., more preferably above 100° C. The drying can for example be performed at temperatures from 120° C. up to 200° C. The drying will normally be performed until substantially all the water is evaporated. Common drying times range from one to up to 30 hours and depend on the drying temperature. The drying step can be accelerated by the use of vacuum.

In case the catalytically active metal is employed on a support, the catalytically active metal can be evenly distributed on the support or can be unevenly distributed on the support. The catalytically active metal can for example be concentrated in the core or in defined layers of the support. The catalytically active metal can be located partially or completely on the inner surface of the support or can be located partially or completely on the outer surface of the support.

In case the catalytically active metal is located completely on the inner surface of the support, the outer surface of the catalyst is identical to the outer surface of the support.

The distribution of the catalytically active metal can be determined with Scanning Electron Microscopy (SEM) and Energy Dispersive X-Ray Spectroscopy (EDXS). The distribution can for example be determined by preparing a cross section of the catalyst. In case the catalyst is a sphere the cross section can be prepared through the center of the sphere. In case the catalyst is a strand, the cross section can be prepared by cutting the strand at a right angle to the axis of the strand. Via backscattered electrons (BSE) the distribution of the catalytically active metal in the catalyst can be visualized. The amount of catalytically active metal can then be quantified via EDXS whereby an acceleration voltage of 20 kV is usually used.

In a preferred embodiment of the invention a catalyst is employed, wherein the catalytically active metal is located in the outer shell of the catalyst. In this embodiment, the catalytically active metal is mainly located in the outer shell of the catalyst.

In one embodiment, the outer shell of the catalyst is the space from the outer surface of the catalyst to a depth of X from the outer surface of the catalyst, wherein X is 15% of the distance from the outer surface of the catalyst to the center of the catalyst. For example, in case a catalyst is employed which is a sphere and has a diameter of 1.5 mm, the outer shell is the space from the outer surface to a depth of 112.5 µm from the outer surface.

In one embodiment, the outer shell of the catalyst is the space from the outer surface of the catalyst to a depth of X from the outer surface of the catalyst, wherein X is 30% of the distance from the outer surface of the catalyst to the center of the catalyst. For example, in case a catalyst is employed which is a sphere and has a diameter of 1.5 mm, the outer shell is the space from the outer surface to a depth of 225 µm from the outer surface.

In one embodiment, the outer shell of the catalyst is the space from the outer surface of the catalyst to a depth of 100 µm from the outer surface of the catalyst.

In one embodiment, the outer shell is the space from the outer surface of the catalyst to a depth of 400 µm, preferably 300 µm, preferably 200 µm from the outer surface of the catalyst.

In a preferred embodiment, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

In a preferred embodiment, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

In a further embodiment of the invention, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 µm from the outer surface of the catalyst.

In a further embodiment of the invention, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 µm, preferably to a depth of 300 µm, preferably to a depth of 200 µm from the outer surface of the catalyst.

In a further embodiment of the invention, a catalyst is employed, wherein the dispersity of the catalytically active metal is on average in the range of 10% to 100%, preferably 30% to 95% (determined with CO-sorption according to DIN 66136-3).

Catalysts in which the catalytically active metal is located in the outer shell of the catalyst can for example be obtained by the deposition-reduction method as described above. The distribution of the catalytically active metal in the outer shell of the catalyst can be effected for example by the choice of the deposition method and/or the choice of the deposition parameters such as temperature, pH and time and the combination of these parameters. A description of the different methods of preparation can for example be found in "Handbook of Heterogeneous Catalysis", edited by G. Ertl, H. Knözinger, J. Weitkamp, Vol 1. Wiley-VCH, 1997. Chapter 2, part 2.2.1.1. Impregnation and Ion Exchange, authors M. Che, O. Clause, and Ch. Marcilly, p. 315-340.

The promotor can be evenly distributed on the support or can be unevenly distributed on the support. In a preferred embodiment, the promotor is distributed in the same way as the catalytically active material on the support.

One embodiment of the invention is directed to the process for the preparation of alpha, beta unsaturated aldehydes of general formula (I)

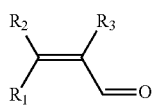

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

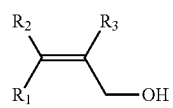

(II)

wherein $R_1$, $R_2$ and $R_3$ have the meaning as given above
in the presence of a catalyst and in the presence of a liquid phase,
  wherein the liquid phase contains 0.1 to less than 25 weight-% water and
  wherein the liquid phase contains at least 25 weight-% of alcohol(s) of general formula (II) and alpha, beta unsaturated aldehyde(s) of general formula (I) and
  wherein the oxidant is oxygen and/or hydrogen peroxide,
  all weight-% based on the total weight of the liquid phase, determined at a temperature of 20° C. and a pressure of 1 bar,
  wherein a catalyst is used which is obtainable by
  a) providing a support
  b) providing a metal compound
  c) depositing the metal compound on the support
  d) optionally calcinating the so obtained catalyst precursor
  e) reducing the catalyst precursor, preferably by treatment of the catalyst precursor with a solution of a reducing agent,
  f) optionally recovering the catalyst.

One embodiment of the invention is directed to the process for the preparation of alpha, beta unsaturated aldehydes of general formula (I)

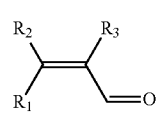

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

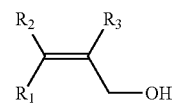

(II)

wherein $R_1$, $R_2$ and $R_3$ have the meaning as given above
in the presence of a catalyst and in the presence of a liquid phase,
  wherein the liquid phase contains 0.1 to less than 25 weight-% water and
  wherein the liquid phase contains at least 25 weight-% of alcohol(s) of general formula (II) and alpha, beta unsaturated aldehyde(s) of general formula (I) and
  wherein the oxidant is oxygen and/or hydrogen peroxide,
  all weight-% based on the total weight of the liquid phase, determined at a temperature of 20° C. and a pressure of 1 bar,
  wherein a catalyst is used, which is obtained by
  a) providing a support
  b) providing a metal compound
  c) depositing the metal compound on the support
  d) optionally calcinating the so obtained catalyst precursor
  e) reducing the catalyst precursor, preferably by treatment of the catalyst precursor with a solution of a reducing agent,
  f) optionally recovering the catalyst.

In a preferred embodiment of these processes, the catalyst comprises platinum as catalytically active metal. In a preferred embodiment of these processes the support is selected from the group consisting of alpha aluminium oxide (α-$Al_2O_3$), beta aluminium oxide (ß-$Al_2O_3$) and gamma aluminium oxide (γ-$Al_2O_3$). In a preferred embodiment of these processes, an alcohol according to formula (II) is used, wherein $R_1$, $R_2$ or $R_3$, independently of one another, are selected from H and $CH_3$, more preferably an alcohol according to formula (II) is used, wherein $R_3$ is H and $R_2$ and $R_1$ are $CH_3$ (=3-methyl-2-buten-1-ol).

One embodiment of the invention is directed to the process for the preparation of alpha, beta unsaturated aldehydes of general formula (I)

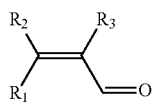

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

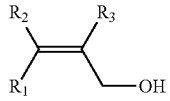

wherein $R_1$, $R_2$ and $R_3$ have the meaning as given above
in the presence of a catalyst and in the presence of a liquid phase,
wherein the liquid phase contains 0.1 to less than 25 weight-% water and
wherein the liquid phase contains at least 25 weight-% of alcohol(s) of general formula (II) and alpha, beta unsaturated aldehyde(s) of general formula (I) and
wherein the oxidant is oxygen and/or hydrogen peroxide,
all weight-% based on the total weight of the liquid phase, determined at a temperature of 20° C. and a pressure of 1 bar,
wherein a catalyst is used, which comprises the catalytically active metal on a support and wherein the catalytically active metal is mainly located in the outer shell of the catalyst.

One embodiment of the invention is directed to the process for the preparation of alpha, beta unsaturated aldehydes of general formula (I)

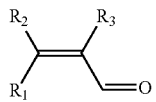

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

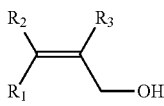

wherein $R_1$, $R_2$ and $R_3$ have the meaning as given above
in the presence of a catalyst and in the presence of a liquid phase,
wherein the liquid phase contains 0.1 to less than 25 weight-% water and
wherein the liquid phase contains at least 25 weight-% of alcohol(s) of general formula (II) and alpha, beta unsaturated aldehyde(s) of general formula (I) and
wherein the oxidant is oxygen and/or hydrogen peroxide,
all weight-% based on the total weight of the liquid phase, determined at a temperature of 20° C. and a pressure of 1 bar,
wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

One embodiment of the invention is directed to the process for the preparation of alpha, beta unsaturated aldehydes of general formula (I)

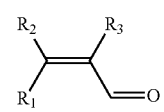

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

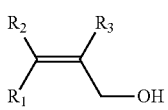

wherein $R_1$, $R_2$ and $R_3$ have the meaning as given above
in the presence of a catalyst and in the presence of a liquid phase,
wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide, all weight-% based on the total weight of the liquid phase, determined at a temperature of 20° C. and a pressure of 1 bar, wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

One embodiment of the invention is directed to the process for the preparation of alpha, beta unsaturated aldehydes of general formula (I)

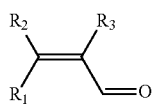

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

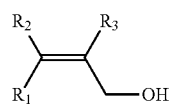

(II)

wherein $R_1$, $R_2$ and $R_3$ have the meaning as given above in the presence of a catalyst and in the presence of a liquid phase, wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide, all weight-% based on the total weight of the liquid phase, determined at a temperature of 20° C. and a pressure of 1 bar, wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 μm from the outer surface of the catalyst.

One embodiment of the invention is directed to the process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase, wherein the liquid phase contains 0.1 to less than 25 weight-% water and wherein the liquid phase contains at least 25 weight-% of alcohol(s) of general formula (II) and alpha, beta unsaturated aldehyde(s) of general formula (I) and wherein the oxidant is oxygen and/or hydrogen peroxide, all weight-% based on the total weight of the liquid phase, determined at a temperature of 20° C. and a pressure of 1 bar, wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 μm, preferably to a depth of 300 μm, preferably to a depth of 200 μm from the outer surface of the catalyst.

In a preferred embodiment of these processes, the catalyst comprises platinum as catalytically active metal. In a preferred embodiment of these processes the support is selected from the group consisting of alpha aluminium oxide (α-$Al_2O_3$), beta aluminium oxide (ß-$Al_2O_3$) and gamma aluminium oxide (γ-$Al_2O_3$). In a preferred embodiment of these processes, an alcohol according to formula (II) is used, wherein $R_1$, $R_2$ or $R_3$, independently of one another, are selected from H and $CH_3$, more preferably an alcohol according to formula (II) is used, wherein $R_3$ is H and $R_2$ and $R_1$ are $CH_3$ (=3-methyl-2-buten-1-ol).

It has surprisingly been found that a catalyst comprising the catalytically active metal on a support, can advantageously be used for the preparation of alpha, beta unsaturated aldehydes of formula (I). In case a catalyst comprising the catalytically active metal on a support is used, specific activities (SA) can be achieved, which are higher than the specific activities that are possible with processes according to the prior art.

Suitable catalysts comprising the catalytically active metal on a support are the ones describe above with all preferred embodiments.

One embodiment of the invention is directed to the process for the preparation of alpha, beta unsaturated aldehydes of general formula (I)

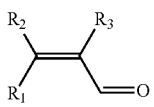

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

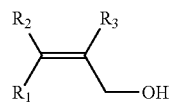

(II)

wherein $R_1$, $R_2$ and $R_3$ have the meaning as given above in the presence of a catalyst, wherein a catalyst is used which is obtainable by a) providing a support
b) providing a metal compound
c) depositing the metal compound on the support
d) optionally calcinating the so obtained catalyst precursor
e) reducing the catalyst precursor, preferably by treatment of the catalyst precursor with a solution of a reducing agent,
f) optionally recovering the catalyst.

One embodiment of the invention is directed to the process for the preparation of alpha, beta unsaturated aldehydes of general formula (I)

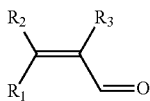

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

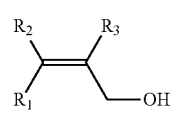

(II)

wherein $R_1$, $R_2$ and $R_3$ have the meaning as given above in the presence of a catalyst, wherein a catalyst is used, which is obtained by a) providing a support
b) providing a metal compound
c) depositing the metal compound on the support
d) optionally calcinating the so obtained catalyst precursor
e) reducing the catalyst precursor, preferably by treatment of the catalyst precursor with a solution of a reducing agent,
f) optionally recovering the catalyst.

In a preferred embodiment of these processes, the oxidation is performed at a temperature from 1 to 250° C.; preferably from 5 to 150° C., more preferably from 20 to 100° C. In a preferred embodiment of these processes, the catalyst comprises platinum as catalytically active metal. In a preferred embodiment of these processes the support is selected from the group consisting of alpha aluminium oxide ($\alpha$-$Al_2O_3$), beta aluminium oxide ($\beta$-$Al_2O_3$) and gamma aluminium oxide ($\gamma$-$Al_2O_3$). In a preferred embodiment of these processes, an alcohol according to formula (II) is used, wherein $R_1$, $R_2$ or $R_3$, independently of one another, are selected from H and $CH_3$, more preferably an alcohol according to formula (II) is used, wherein $R_3$ is H and $R_2$ and $R_1$ are $CH_3$ (=3-methyl-2-buten-1-ol). In a preferred embodiment of these processes the oxidant is oxygen and/or hydrogen peroxide.

Suitable catalysts comprising the catalytically active metal on a support are the ones describe above with all preferred embodiments.

A further aspect of the invention is directed to the process for the preparation of alpha, beta unsaturated aldehydes of general formula (I)

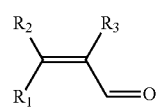

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

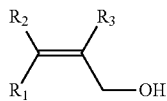

(II)

wherein $R_1$, $R_2$ and $R_3$ have the meaning as given above in the presence of a catalyst, wherein a catalyst is used, which comprises the catalytically active metal on a support and wherein the catalytically active metal is mainly located in the outer shell of the catalyst.

A further aspect of the invention is therefore is directed to the process for the preparation of alpha, beta unsaturated aldehydes of general formula (I)

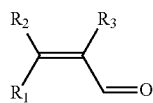

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

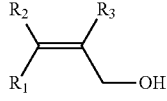

(II)

wherein $R_1$, $R_2$ and $R_3$ have the meaning as given above in the presence of a catalyst, wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

A further aspect of the invention is therefore is directed to the process for the preparation of alpha, beta unsaturated aldehydes of general formula (I)

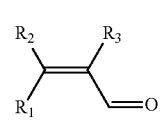

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

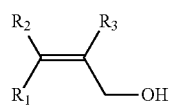

(II)

wherein $R_1$, $R_2$ and $R_3$ have the meaning as given above in the presence of a catalyst, wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

A further aspect of the invention is therefore is directed to the process for the preparation of alpha, beta unsaturated aldehydes of general formula (I)

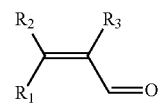

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

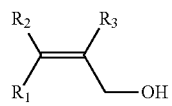

(II)

wherein $R_1$, $R_2$ and $R_3$ have the meaning as given above in the presence of a catalyst, wherein a catalyst is used, which comprises the catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 μm from the outer surface of the catalyst.

A further aspect of the invention is therefore is directed to the process for the preparation of alpha, beta unsaturated aldehydes of general formula (I)

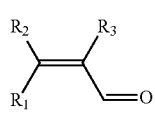

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

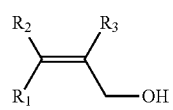

(II)

wherein $R_1$, $R_2$ and $R_3$ have the meaning as given above in the presence of a catalyst, wherein a catalyst is used, which comprises the catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 μm, preferably to a depth of 300 μm, preferably to a depth of 200 μm from the outer surface of the catalyst.

In a preferred embodiment of these processes, the oxidation is performed at a temperature from 1 to 250° C.; preferably from 5 to 150° C., more preferably from 20 to 100° C. In a preferred embodiment of these processes, the catalyst comprises platinum as catalytically active metal. In a preferred embodiment of these processes the support is selected from the group consisting of alpha aluminium oxide (α-$Al_2O_3$), beta aluminium oxide (ß-$Al_2O_3$) and gamma aluminium oxide (γ-$Al_2O_3$). In a preferred embodiment of these processes, an alcohol according to formula (II) is used, wherein $R_1$, $R_2$ or $R_3$, independently of one another, are selected from H and $CH_3$, more preferably an alcohol according to formula (II) is used, wherein $R_3$ is H and $R_2$ and $R_1$ are $CH_3$ (=3-methyl-2-buten-1-ol). In a preferred embodiment of these processes the oxidant is oxygen and/or hydrogen peroxide.

Process Mode

The embodiments of the process mode described hereinafter can suitably be applied in all processes described above.

The process according to the invention can be performed in reaction vessels customary for such reactions, the reaction being configurable in a continuous, semi-batch or batch-wise mode. In general, the particular reactions will be performed under atmospheric pressure. The process may, however, also be performed under reduced or increased pressure.

The process according to the invention can be performed under pressure, preferably under a pressure between above 1 bar and 15 bar (absolute), preferably between above 1 bar and 10 bar (absolute).

In case oxygen is used as the oxidant, the process according to the invention can be performed at a partial pressure of oxygen from 0.1 to 15 bar, preferably from 0.2 to 10 bar, preferably from 0.2 to 8 bar, more preferably from 0.2 to 5 bar, more preferably from 1 to 3, preferably from 1 to 2.5, more preferably from 1.2 to 2 bar.

In a preferred embodiment of the invention the process is conducted as a batch process. In a preferred embodiment of the invention the process is conducted as a semi-batch process. In a preferred embodiment of the invention the process is conducted as a continuous process.

In a preferred embodiment of the invention the process is conducted with a fixed-bed catalyst. In case the process according to the invention is conducted with a fixed-bed catalyst, suitable fixed-bed reactors can be selected from the group consisting of trickle-bed reactors, bubble-packed reactors, multi-tubular reactors and plate reactors.

The process according to the invention can be conducted in one fixed-bed reactor or can preferably be conducted in more than one, preferably more than two, more preferably more than three, preferably three to five fixed-bed reactors. The one or more fixed-bed reactors can be arranged in series or in parallel.

The process according to the invention can be conducted at common values of weight hourly space velocity (WHSV), defined as the hourly mass flow of the process feed (in kg/h) per catalyst (in kg). The process can for example be performed at WHSV values of 1 to 20000, preferably 10 to 10000, preferably 20 to 5000, preferably 20 to 500, more preferably from 50 to 100 kg/kg/h.

The process according to the invention can be conducted in one or more fixed-bed reactor(s) with or without heat exchange. In one embodiment of the invention, the fixed-bed reactor(s) can be operated so that a constant temperature is held over one, some or all fixed-bed reactors. In one embodiment of the invention, the fixed-bed reactor(s) can be operated so that a defined temperature gradient is maintained over one, some or all fixed-bed reactors without heat addition or removal. In one embodiment of the invention, the fixed-bed reactor(s) can be operated with a temperature controlled profile, wherein a defined temperature profile is maintained over one, some or all fixed-bed reactors with internal or external heat addition or removal.

In a preferred embodiment of the invention the process is conducted in a trickle-bed reactor with a fixed-bed catalyst. In one embodiment of the invention, the process is conducted with more than one, preferably more than two, more preferably more than three trickle-bed reactors, which are arranged in series or in parallel, preferably in series. In one embodiment, the process is conducted with three to five trickle-bed reactors, which are arranged in series. In one embodiment, one or more, preferably each of the trickle-bed reactors can be provided with a liquid recycle stream.

In a preferred embodiment of the trickle-bed reactor, the components of the reaction can be inserted to the reactor concurrently, meaning that the liquid phase(s) and the gas phase comprising the oxidant oxygen, are inserted to the reactor at the same side, preferably at the top of the reactor.

In one embodiment of the invention the process is conducted in a bubble-packed reactor with a fixed-bed catalyst. In one embodiment of the invention, the process is conducted with more than one, preferably more than two, more preferably more than three bubble-packed reactors, which are arranged in series or in parallel, preferably in series. In one embodiment, the process is conducted with three to five bubble-packed reactors, which are arranged in series.

In one embodiment of the bubble-packed reactor, the components of the reaction can be inserted in the reactor concurrently, meaning that the liquid phase(s) and the gas phase comprising the oxidant oxygen, are inserted to the reactor at the same side, preferably at the bottom of the reactor. In one embodiment of the bubble-packed reactor, the components of the reaction can be inserted in the reactor countercurrently, meaning that the liquid phase(s) and the gas phase comprising the oxidant oxygen, are inserted to the reactor at opposite sides. In one embodiment, the liquid phase(s) are inserted to the reactor at the bottom of the reactor, whereas the gas phase comprising oxygen as oxidant is inserted at the top of the reactor. In one embodiment, the liquid phase(s) are inserted to the reactor at the top of the reactor, whereas the gas phase comprising oxygen as oxidant is inserted at the bottom of the reactor.

In a preferred embodiment of the invention the process is conducted as a slurry process. The process can be conducted in a slurry-based system as stirred tank reactor or slurry bubble column.

The reaction is carried out by contacting alcohol(s) of general formula (II), water, catalyst, the oxidant and optional components, such as for example one or more solvent(s), under suitable reaction conditions.

These components can in principle be contacted with one another in any desired sequence. For example, the alcohol(s) of general formula (II), if appropriate dissolved in water or a solvent or in dispersed form, can be initially charged and admixed with the catalyst or, conversely, the catalytic system can be initially charged and admixed with the alcohol(s) of general formula (II) and water. Alternatively, these components can also be added simultaneously to the reaction vessel.

As an example for a batch-wise slurry process a stirred tank reactor can be used where the catalyst, the reactant, water, hydrogen peroxide (if used as oxidant) and optionally solvent are loaded. In case oxygen is used as oxidant, the reactor is then pressurized with oxygen. The reaction is then performed until the desired conversion is achieved.

As an example for a batch-wise slurry process a stirred tank reactor can be used where the catalyst, the reactant(s), if appropriate dissolved in water or solvent or in dispersed form, water, hydrogen peroxide (if used as oxidant) and optionally one or more solvent(s) are loaded. In case oxygen is used as oxidant, the reactor is then pressurized with oxygen. The reaction is then performed until the desired conversion is achieved.

As an example for a semi-batch process a stirred tank reactor can be used where the catalyst, the reactant(s), water, hydrogen peroxide (if used as oxidant) and optionally solvent are loaded. In case oxygen is used as an oxidant, the oxygen is then continuously fed to the reactor until the desired conversion is achieved. As another example for a semi-batch process a fixed bed catalyst in a trickle-bed reactor can be used. The solution of reactant(s), water, hydrogen peroxide (if used as oxidant), optionally comprising solvent, are then pumped in a loop over the catalyst. In case oxygen is used as oxidant, oxygen is passed as a continuous stream through the reactor. In one embodiment of the invention the oxygen can be added in excess, the excess being released to the off gas, alternatively the oxygen can be added in an amount required to replenish the consumed oxygen.

As an example for a continuous slurry process, a continuous stirred tank reactor can be used in which the catalyst is present. The solution of the reactant(s), water, optionally comprising solvent and the oxidant (oxygen and/or hydrogen peroxide) are added continuously. In case oxygen is used as oxidant, it can be added in excess, off-gas can then be taken out continuously. In an alternative embodiment, oxygen can be added in an amount to replenish the consumed oxygen. The liquid reaction product can be taken off continuously through a filter in order to keep the catalyst in the reactor.

In a further example for a continuous fixed bed process, both the solution of reactant(s) and the oxidant (oxygen and/or hydrogen peroxide) are continuously fed to a trickle bed reactor containing the catalyst. In this case, it is possible to partly or fully recycle the gas (in case oxygen is used as oxidant) and/or the liquid back to the reactor in order to achieve the desired conversion of reactant(s) and/or oxygen (in case oxygen is used as oxidant).

In a preferred embodiment, the process according to the invention is carried out in a continuous mode.

It has surprisingly been found that the process of the invention leads to selectivities of the alpha, beta unsaturated aldehyde(s) (based on the alcohol of general formula (II)) in the range of over 90%, preferably over 93%, preferably over 95%, preferably over 97% more preferably over 99%.

Preferably the process according to the invention is conducted until a conversion of the alcohol of general formula (II) in the range of 10 to 99.99%, preferably in the range of 30 to 95%, and most preferably in the range of 50 to 80% is obtained.

Preferably the process according to the invention is performed at a temperature in the range from 1 to 250° C., preferably in the range from 5 to 150° C., preferably in the range from 20 to 100° C., in the range from 20° C. to 70° C., more preferably in the range from 25° C. to 80° C., preferably in the range from 30 to 70° C. and more preferably in the range of 35 to 50° C. In one embodiment of the invention, the process is performed at a temperature in the range of 40 to 80° C.

The obtained crude product(s) may be subjected to conventional purification measures, including distillation or chromatography or combined measures. Suitable distillation devices for the purification of the product(s) include, for example, distillation columns, such as tray columns optionally equipped with bubble cap trays, sieve plates, sieve trays, packages or filler materials, or spinning band columns, such as thin film evaporators, falling film evaporators, forced circulation evaporators, wiped-film (Sambay) evaporators, etc. and combinations thereof.

The invention is further illustrated by the following non-limiting examples:

EXAMPLES—CATALYST PREPARATION

Example C1

Step a): Support: 50 g of aluminium oxide (gamma-$Al_2O_3$ strands with a mean diameter of 1.5 mm (commercially available from Exacer s.r.l. Italy), was heated to 550° C. for 4 hours and maintained at 550° C. for 1 hour.

Step b): 6.68 g of a 15.4 wt. % $Pt(NO_3)_2$ solution in 10 weight % nitric acid and 1.29 g of $Bi(NO_3)_3$ were added to 95.21 g water at room temperature.

Step c): A flask was equipped with 50 g of aluminium oxide obtained in step a) and immersed with the Pt/Bi solution obtained in step b) and stirred for 0.5 hours at 70 mbar while the mixture was heated to 80° C. At 80° C. the solvent was removed within 30 minutes.

Drying was performed in a rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor obtained in step d) were added to 400 g of water and heated to 60° C. An aqueous sodium formate solution was prepared (34.87 g of sodium formate (97%) plus 88.38 g water) and added dropwise to the catalyst precursor over a time period of 10 minutes. The reaction mixture was maintained at 60° C. for 140 minutes and then left to cool to room temperature under $N_2$.

The catalyst was recovered by filtration and washed with water to a conductivity below 170 μS/cm and subsequently dried at 80° C. for 4 hours. The so obtained catalyst displayed a Pt content of 1.4 weight % and a molar ratio of Pt:Bi of 1:0.5. The distribution of the catalytically active metal Pt was determined with SEM-EDXS in a cross section of the strands: the majority of the Pt was located within 100 μm from the outer surface of the catalyst.

Example C2

Example $C_1$ was repeated, with the following modification of step c):

Step c): A flask was equipped with 50 g of aluminium oxide obtained in step a) and immersed with the Pt/Bi solution obtained in step b) and stirred for 10 minutes at 70 mbar. The catalyst precursor was recovered by filtration.

The so obtained catalyst displayed a Pt content of 1.4 weight % and a molar ratio of Pt:Bi of 1:0.5, The distribution of the catalytically active metal Pt was determined with SEM-EDXS in a cross section of the strands: the majority of the Pt was located within 100 μm from the outer surface of the catalyst.

Example C3

Step a): Support: 50 g of aluminium oxide (gamma $Al_2O_3$ strands with a diameter of 1.5 mm (commercially available from Exacer s.r.l. Italy) was heated to 550° C. for 4 hours and maintained at 550° C. for 1 hour.

Step b): 6.63 g of a 15.4 weight % $Pt(NO_3)_2$ solution in 10 weight % nitric acid and 5.09 g of $Bi(NO_3)_3$ were added to 29.6 g water at room temperature.

Step c): A flask was equipped with 50 g of aluminium oxide obtained in step a) and rotated at 70 mbar. The Pt/Bi solution obtained in step b) was added via a dropping funnel to the injection nozzle and sprayed onto the support. The deposition step was conducted under mixing for 30 minutes at room temperature. Drying was performed in the rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor were added to 400 g of water and heated to 60° C. An aqueous sodium formate solution was prepared (34.87 g of sodium formate (97%) plus 88.38 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 170 μS/cm and subsequently dried at 80° C. for 4 hours. The so obtained catalyst displayed a Pt content of 1.6 weight % and a molar ratio of Pt:Bi of 1:2. The distribution of the catalytically active metal Pt was determined with SEM-EDXS in a cross section of the strands: the majority of the Pt was located within 100 μm from the outer surface of the catalyst.

Example C4

Example $C_3$ was repeated, with the following modification in step b): 2.55 g (instead of 5.09 g) of $Bi(NO_3)_3$ were added to the solution.

The so obtained catalyst displayed a Pt content of 1.6 weight % and a molar ratio of Pt:Bi of 1:1. The distribution of the catalytically active metal Pt was determined with SEM-EDXS in a cross section of the strands: the majority of the Pt was located within 100 μm from the outer surface of the catalyst.

Example C5

Example $C_3$ was repeated, with the following modification in step b): 1.27 g (instead of 5.09 g) of $Bi(NO_3)_3$ were added to the solution.

The so obtained catalyst displayed a Pt content of 1.6 weight % and a molar ratio of Pt:Bi of 1:0.5. The distribution of the catalytically active metal Pt was determined with SEM-EDXS in a cross section of the strands: the majority of the Pt was located within 400 μm from the outer surface of the catalyst.

Example C6

Step a): 40 g of gamma-aluminium oxide (strands with a diameter of 1.5 was heated to 550° C. for 4 hours and maintained at 550° C. for 1 hour.

Step b): A 15.7 wt. % $Pt(NO_3)_2$ solution in 10 weight % nitric acid was prepared.

Step c): A rotary plate was equipped with 40 g of aluminium oxide obtained in step a), rotated and heated to 100° C. 15.95 g of a 15.7 wt. % $Pt(NO_3)_2$ solution in 10 weight % nitric acid was sprayed onto the support with an injection nozzle within 1 hour and 6 minutes. After the addition was complete the mixture was rotated for an additional 10 minutes on the hot rotary plate and subsequently dried.

Step d): The so obtained catalyst precursor was placed in a muffle furnace and heated to 450° C. over a time period of 3 hours. The temperature of 450° C. was maintained for 1 hour.

Step e): Reduction of the catalyst precursor was performed by treatment of the catalyst precursor with a solution of a reducing agent. 41.97 g of the catalyst precursor was added to 399.94 g of water and heated to 60° C. An aqueous sodium formate solution was prepared (29.32 g of sodium formate plus 74.13 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 132.5 µS/cm and subsequently dried at 80° C. for 4.5 hours.

The so obtained catalyst displayed Pt content of 2.6 weight %. The distribution of the catalytically active metal Pt was determined with SEM-EDXS in a cross section of the strands: the majority of the Pt was located within 100 µm from the surface of the catalyst.

FIGS. 1 and 2 display the Pt distribution in the catalyst of example C6. In FIG. 2 the Y-axis shows the local Pt-concentration in weight % measured by EDX, while the X-axis shows the position at which the measurement was taken. The distances are taken along the dotted line in FIG. 1 and the zero point is at the left side.

EXAMPLES—PROCESS

Gas Chromatographic Analysis:
GC-system and separation method:
GC-system: Agilent 7890A
GC-Column: RTX-200 (60 m (Length), 0.32 mm (ID), 1.0 µm (Film))
Temperature program: 10 minutes at 60° C., 60° C. to 280° C. in 6° C./min, 10 minutes at 280° C.

Examples 1-3: Oxidation of 3-Methyl-2-buten-1-ol at 40° C. with $O_2$ on Platinum Supported on Aluminia Under $O_2$ Pressure A double jacketed reactor (length: 115 cm, internal diameter: 6 mm) was charged with 23 g of Pt/$Al_2O_3$ (10 w/w.-% Pt on $Al_2O_3$ obtained from Alfa Aesar). The remaining reactor volume was filled with inert material (glass spheres, 5 mm in diameter, to a height of ca. 8 cm at the bottom of the reactor and to a height of 4 cm at the top of the reactor). Under 1 bar $N_2$ atmosphere, a 270 ml stirred-vessel was filled with a 150 g of a mixture of 3-Methyl-2-buten-1-ol and water (composition see Table 1) and the mixture was metered through the reactor by using a metering pump at a flow rate of 2 kg/h. The reactor temperature was adjusted at 40° C. using a thermostat and set under constant $O_2$ pressure of 2 bar ($O_2$ flow between 4 and 4.5 l/h). Samples were taken hourly from the stirred-vessel and the mixture was quantitatively analyzed by GC using dioxane as internal standard. Table 1 sums up the results after 4 hours of reaction time. Conversion and selectivity are based on the weight percentages of all detected components as determined by GC. 3-Methyl-2-buten-1-ol ("Prenol") was obtained from BASF.

TABLE 1

| Example | 3-Methyl-2-buten-1-ol (weight-% based on the total liquid phase) | Water (weight-% based on the total liquid phase) | Conversion after 4 hours | Selectivity to aldehyde based on starting alcohol/% | Space-Time-Yield [g/l/h] |
|---|---|---|---|---|---|
| 1 | 85 | 15 | 47 | 99 | 86 |
| 2 | 90 | 10 | 48 | 99 | 92.6 |
| 3 | 95 | 5 | 43 | 99 | 86.8 |

With the process according to the invention, 3-Methyl-2-butenal (prenal) could surprisingly be obtained at a selectivity of 99%.

With the process according to the invention a substantial increase in the space-time-yield (STY) could be obtained as compared to the prior art. The time-space-yield for the oxidation of 3-methyl-2-butenol to 3-methyl-2-butenal with 5% hydrogen peroxide as oxidant and Pt black as catalyst according to entry 7 of Table 1 of Chem. Commun. (2007) 4399-4400 is 30 g/l/h.

Examples 4 and 5: Oxidation of 3-Methyl-2-buten-1-ol at 50° C. with $O_2$ on Platinum Supported on Alumina Under $O_2$ Pressure A double jacketed reactor (length: 41 cm, internal diameter: 15 mm) was charged with 23 g of catalyst obtained according to example C1 for example 4 and C2 for example 5. The remaining reactor volume was filled with inert material (glass spheres, 5 mm in diameter, to a height of about 10.5 cm at the bottom of the reactor and to a height of 7.5 cm at the top of the reactor). Under 1 bar $N_2$ atmosphere, a 270 mL stirred-vessel was filled with a 150 g mixture of 3-Methyl-2-buten-1-ol and water (composition see Table 2) and the mixture was metered through the reactor by using a metering pump at a flow rate of 12 kg/h. The reactor temperature was adjusted at 50° C. using a thermostat and set under constant $O_2$ pressure of 2 bar ($O_2$ flow set a 20 l/h). Samples were taken hourly from the stirred-vessel and the mixture was quantitatively analyzed by GC using dioxane as internal standard. Table 2 sums up the results after 4 hours of reaction time. Conversion and selectivity are based on the weight percentages of all detected components as determined by GC. 3-Methyl-2-buten-1-ol ("Prenol") was obtained from BASF.

TABLE 2

| Example | Catalyst according to example | 3-Methyl-2-buten-1-ol (weight-% based on the total liquid phase) | Water (weight-% based on the total liquid phase) | Conversion after 4 hours/% | Selectivity to aldehyde based on starting alcohol/% | Space-Time-Yield [g/l/h] |
|---|---|---|---|---|---|---|
| 4 | C1 | 90 | 10 | 82.5 | 99 | 618 |
| 5 | C2 | 90 | 10 | 89.6 | 99 | 730 |

The invention claimed is:
1. A process for the preparation of alpha, beta unsaturated aldehydes of general formula (I)

wherein $R_1$, $R_2$ and $R_3$, independently of one another, are selected from
hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;
by oxidation of alcohols of general formula (II) out at a temperature of 20° C. to 100° C.,

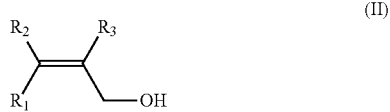

wherein $R_1$, $R_2$ and $R_3$ have the meaning as given above in the presence of a catalyst and in the presence of a liquid phase,
wherein the liquid phase contains 0.1 to less than 25 weight-% water and
wherein the liquid phase contains at least 25 weight-% of alcohol(s) of general formula (II) and alpha, beta unsaturated aldehyde(s) of general formula (I) and
wherein the oxidant is oxygen and/or hydrogen peroxide,
wherein the oxidation is carried out at a temperature of 20° C. to 100° C.,
all weight-% based on the total weight of the liquid phase determined at a temperature of 20° C. and a pressure of 1 bar.

2. The process according to claim 1, wherein the alcohol according to formula (II) is used, wherein $R_1$, $R_2$ or $R_3$, independently of one another, are selected from H and $CH_3$.

3. The process according to claim 1, wherein the alcohol according to formula (II) is used, wherein $R_3$ is H and $R_2$ and $R_1$ are $CH_3$.

4. The process according to claim 1, wherein the liquid phase contains 0.5 to 20 weight-%, water based on the total weight of the liquid phase.

5. The process according to claim 1, wherein the liquid phase contains 1.0 to 15 weight-% water based on the total weight of the liquid phase.

6. The process according to claim 1, wherein the liquid phase contains less than 75 weight-% solvent based on the total weight of the liquid phase.

7. The process according to claim 1, wherein the liquid phase contains less than 50 weight-% based on the total weight of the liquid phase.

8. The process according to claim 1, wherein the liquid phase contains less than 10 weight-% solvent based on the total weight of the liquid phase.

9. The process according to claim 1 wherein the liquid phase contains at least 30 weight-% of alcohols of general formula (II) and alpha, beta unsaturated aldehydes of general formula (I), based on the total weight of the liquid phase.

10. The process according to claim 1 wherein the liquid phase contains at least 70 weight-% of alcohols of general formula (II) and alpha, beta unsaturated aldehydes of general formula (I), based on the total weight of the liquid phase.

11. The process according to claim 1 wherein the liquid phase contains at least 95 weight-% of alcohols of general formula (II) and alpha, beta unsaturated aldehydes of general formula (I), based on the total weight of the liquid phase.

12. The process according to claim 1, wherein the oxidation is carried out in the presence of a catalyst which comprises at least one catalytically active metal selected from the group consisting of platinum, palladium and gold.

13. The process according to claim 1, wherein the catalyst comprises as catalytically active metal platinum.

14. The process according to claim 1 wherein the catalytically active metal is on a support.

15. The process according to claim 1, wherein the oxidation is carried out at a temperature of 20° C. to 70° C.

16. The process according to claim 1, wherein the oxidation is carried out under a partial pressure of oxygen between 0.2 and 8 bar.

17. The process according to claim 1 wherein the catalyst comprises iron, cobalt, nickel, ruthenium, rhodium, palladium, osmium, iridium, platinum, or gold.

* * * * *